(12) United States Patent
He et al.

(10) Patent No.: US 11,656,298 B2
(45) Date of Patent: May 23, 2023

(54) DEEP PARALLEL FAULT DIAGNOSIS METHOD AND SYSTEM FOR DISSOLVED GAS IN TRANSFORMER OIL

(71) Applicant: WUHAN UNIVERSITY, Hubei (CN)

(72) Inventors: Yigang He, Hubei (CN); Xiaoxin Wu, Hubei (CN); Jiajun Duan, Hubei (CN); Yuanxin Xiong, Hubei (CN); Hui Zhang, Hubei (CN)

(73) Assignee: WUHAN UNIVERSITY, Hubei (CN)

( * ) Notice: Subject to any disclaimer, the term of this patent is extended or adjusted under 35 U.S.C. 154(b) by 200 days.

(21) Appl. No.: 17/160,415

(22) Filed: Jan. 28, 2021

(65) Prior Publication Data
US 2021/0278478 A1    Sep. 9, 2021

(30) Foreign Application Priority Data
Mar. 2, 2020    (CN) .......................... 202010134616.3

(51) Int. Cl.
| | | |
|---|---|---|
| *G01R 31/62* | (2020.01) | |
| *G01N 33/00* | (2006.01) | |
| *G06N 3/045* | (2023.01) | |
| *G06N 3/044* | (2023.01) | |

(52) U.S. Cl.
CPC ......... *G01R 31/62* (2020.01); *G01N 33/0004* (2013.01); *G06N 3/045* (2023.01); *G06N 3/044* (2023.01)

(58) Field of Classification Search
CPC .... G01R 31/62; G01R 31/00; G01N 33/0004; G06N 3/0454; G06N 3/0445; G06N 3/08; Y04S 10/50
See application file for complete search history.

(56) References Cited

FOREIGN PATENT DOCUMENTS

| CN | 108037378 A | * | 5/2018 | ............. G01R 31/00 |
|---|---|---|---|---|
| CN | 109242205 A | * | 1/2019 | |
| CN | 109885948 A | * | 6/2019 | ............. G06F 17/50 |
| CN | 110441500 A | * | 11/2019 | ............. G01N 33/28 |

* cited by examiner

*Primary Examiner* — Alvaro E Fortich
*Assistant Examiner* — Dilara Sultana
(74) *Attorney, Agent, or Firm* — JCIPRNET

(57) ABSTRACT

The disclosure provides a deep parallel fault diagnosis method and system for dissolved gas in transformer oil, which relate to the field of power transformer fault diagnosis. The deep parallel fault diagnosis method includes: collecting monitoring information of dissolved gas in each transformer substation and performing a normalizing processing on the data; using the dissolved gas in the oil to build feature parameters as the input of the LSTM diagnosis model, and performing image processing on the data as the input of the CNN diagnosis model; building the LSTM diagnosis model and the CNN diagnosis model, respectively, and using the data set to train and verify the diagnosis models according to the proportion; and using the DS evidence theory calculation to perform a deep parallel fusion of the outputs of the softmax layers of the two deep learning models.

16 Claims, 4 Drawing Sheets

DEEP PARALLEL FAULT DIAGNOSIS METHOD AND SYSTEM FOR DISSOLVED GAS IN TRANSFORMER OIL

CROSS-REFERENCE TO RELATED APPLICATION

This application claims the priority benefit of China application serial no. 202010134616.3, filed on Mar. 2, 2020. The entirety of the above-mentioned patent application is hereby incorporated by reference herein and made a part of this specification.

BACKGROUND

Technical Field

The disclosure relates to the field of power transformer fault diagnosis, and more specifically, relates to a deep parallel fault diagnosis method and system for dissolved gas in transformer oil.

Description of Related Art

With the continuous development of computer storage and sensor technology, online monitoring data of power transformers will exhibit a fast-growing trend. Since the power transformer is a crucial equipment in the power system, its operation state directly affects the safety and stability of the entire power grid. Therefore, the integrated use of advanced technologies such as artificial intelligence and big data to perform fault diagnosis and state prediction on the online monitoring data of large-capacity power transformers is a major research hotspot to guide transformer operation, maintenance and repair related work. The dissolved gas analysis (DGA) is an online monitoring technology that analyzes the composition and content of dissolved gas in transformer insulating oil. At present, a large number of studies have been conducted on conventional diagnosis methods based on DGA data. Conventional ratio methods (such as the IEC ratio method, the Rogers ratio method and the Doernenburg ratio method) are simple and easy to implement and have been widely used in engineering practice. However, there are still some problems, such as over-absolute diagnosis boundaries and missing codes. Conventional intelligent methods still have certain limitations when they are promoted and applied due to the insufficient capacity in learning ability, processing efficiency, feature extraction and the like. For example, neural networks tend to fall into local optimal solutions; the K-nearest neighbor method has low computational efficiency in high-dimensional spaces; the support vector machine is essentially a two-classifier, and it is more less efficient in dealing with multi-classification problems, and the like. There are related researches on the diagnosis combining conventional ratio methods and conventional intelligent methods, but the effect is still not ideal enough. In recent years, because deep learning has a strong ability to extract complex nonlinear features, it is introduced into the field of transformer fault diagnosis, and its fault diagnosis accuracy has been significantly improved compared with conventional machine learning diagnosis models. For example, the current new fault diagnosis method based on ReLU-DBN, which uses the uncoded ratio of DGA data as the input matrix, has greatly improved accuracy compared with conventional methods. There are also convolutional neural network-based (CNN-based) transformer internal fault diagnosis, which uses CNN to enhance the performance of differential protection, and the effectiveness of the method is verified through different reliability indicators.

Convolutional neural networks (CNNs) and recurrent neural networks (RNN) are the two most widely used frameworks in deep learning. CNN has been applied more maturely in the fields of visual recognition, image processing, and fault diagnosis. As an improved model of RNN, long short-term memory (LSTM) is used to make up for the defects of long-term memory loss, gradient dissipation or explosion in the process of feedback information of RNN models. Nowadays, it is widely used in various fields such as speech recognition, video classification and stock prediction, and has achieved good effects.

Therefore, how to introduce CNN and LSTM into transformer DGA fault diagnosis model building to improve the fault diagnosis accuracy is a technical problem that needs to be solved urgently.

SUMMARY

In view of the above defects or improvement requirements of the conventional technology, the disclosure provides a deep parallel fault diagnosis method and system for dissolved gas in transformer oil to solve the technical problem of how to introduce CNN and LSTM into transformer DGA fault diagnosis model building, thereby improving the fault diagnosis accuracy.

In order to achieve the above, according to one aspect of the disclosure, a deep parallel fault diagnosis method for dissolved gas in transformer oil is provided, including:

(1) obtaining multiple groups of monitoring data of dissolved gas in each transformer oil, analyzing a dissolved gas content in each of the groups of monitoring data, obtaining a corresponding fault type label, performing a normalizing processing on each of the groups of monitoring data, and forming a target data set by combining the normalized groups of monitoring data with the corresponding fault type label;

(2) dividing the target data set into a first training set and a first verification set, training a long short-term memory (LSTM) diagnosis model with the first training set, and verifying the trained LSTM diagnosis model with the first verification set;

(3) performing image processing on each group of data in the target data set to obtain an image data set, dividing the image data set into a second training set and a second verification set, training a convolutional neural network (CNN) diagnosis model with the second training set, and verifying the trained CNN diagnosis model with the second verification set; and (4) performing a deep parallel fusion on outputs of softmax layers of the trained LSTM diagnosis model and the trained CNN diagnosis model, respectively, and outputting a final diagnosis result according to a maximum confidence principle.

Preferably, the groups of monitoring data of the dissolved gas in each transformer oil are $data_i = \{a_{i,1}, a_{i,2}, a_{i,j}, \ldots, a_{i,j}, \ldots, a_{i,N}, s_i\}$ $i \in [1,K]$, where K is K groups of monitoring data of the dissolved gas, $a_{i,j}$ is a content of the $j(j \in [1,N])$-th gas parameter in the i-th group of monitoring data of the dissolved gas, $s_i$ is a transformer state corresponding to the i-th group of monitoring data of the dissolved gas, and N is the number of gas types.

Preferably, data obtained after normalization is $data_i' = \{b_{i,1}, b_{i,2}, \ldots, b_{i,j}, \ldots, b_{i,N}, s_i\}$ $i \in [1,K]$, where K is K groups of monitoring data of the dissolved gas, $b_{i,j}$ is a normalized value of the content of the j(j∈[1, N])-th gas parameter in the i-th group of monitoring data of the dissolved gas, $s_i$ is the transformer state corresponding to the i-th group of monitoring data of the dissolved gas, and N is the number of gas types.

Preferably, the LSTM diagnosis model includes an input layer, an LSTM layer, a fully connected layer, the softmax layer, and a classification output layer. The LSTM layer has multiple hidden units, and a state activation function of the hidden units is tanh, and a gate activation function of the hidden units is sigmoid, and the softmax layer takes an output of the fully connected layer in the LSTM diagnosis model as an input vector and obtains a diagnosis support degree of the LSTM diagnosis model for a fault label.

Preferably, a diagnosis support degree output by the softmax layer in the LSTM diagnosis model for a fault label is obtained by $$\text{Softmax}(x_1) = \frac{1}{\sum_{i=1}^{N} e^{\theta_i^T x_1}} \begin{bmatrix} e^{\theta_1^T x_1} \\ e^{\theta_2^T x_1} \\ \vdots \\ e^{\theta_N^T x_1} \end{bmatrix},$$

where $x_1$ represents the output of the fully connected layer in the LSTM diagnosis model, $\theta_i$, i=1, 2, ..., N is a weight matrix of the softmax layer in the LSTM diagnosis model, and Softmax is an activation function.

Preferably, performing image processing on each group of data in the target data set to obtain the image data set in the step (3) includes:

performing image processing on each group of data in the target data set, presenting differences of the data in image with color to obtain an image data set A and presenting differences of the data in image with height to obtain an image data set B, respectively. The image data set A is expressed as $\text{data}_i'' = \{c_i, s_i\}$ i∈[1,K], and the image data set B is expressed as $\text{data}_i''' = \{d_i, s_i\}$ i∈[1,K], where K is K groups of monitoring data of the dissolved gas, $c_i$ is an image of a parameter conversion of the i-th group of monitoring data of the dissolved gas in the image data set A, $d_i$ is an image of a parameter conversion of the i-th group of monitoring data of the dissolved gas in the image data set B, and $s_i$ is the transformer state corresponding to the i-th group of monitoring data of the dissolved gas.

Preferably, the softmax layer in the CNN diagnosis model takes an output of a fully connected layer in the CNN diagnosis model as an input vector and obtains a diagnosis support degree for a fault label by $$\text{Softmax}(x_2) = \frac{1}{\sum_{i=1}^{N} e^{\theta_i'^T x_2}} \begin{bmatrix} e^{\theta_1'^T x_2} \\ e^{\theta_2'^T x_2} \\ \vdots \\ e^{\theta_N'^T x_2} \end{bmatrix},$$

where $x_2$ represents the output of the fully connected layer in the CNN diagnosis model, $\theta_i'$, i=1, 2, ..., N is a weight matrix of the softmax layer in the CNN diagnosis model, and Softmax is an activation function.

Preferably, the step (4) includes:

(4.1) obtaining diagnosis support degrees of the softmax layers of the LSTM diagnosis model and the CNN diagnosis model for fault labels corresponding to the same group of monitoring data to be diagnosed: $\xi_{k,\gamma} = \xi_{k,1}, \xi_{k,2}, \ldots, \xi_{k,l}$, where the value of k represents different diagnosis models, l is the total number of fault labels, and γ=1, 2, ..., l;

(4.2) taking different diagnosis models k as rows and the diagnosis support degrees $\xi_{k,\gamma}$ as columns to form a support degree matrix $\{(H_\gamma, \xi_{k,\gamma}), k=1, 2, \gamma=1, \ldots, l\}$, where each element of the support degree matrix represents that the support degree of the k-th diagnosis model for a fault label $H_\gamma$ is $\xi_{k,\gamma}$;

(4.3) treating each column in the support degree matrix as an identification framework Θ of a DS evidence theory, thus $\Theta = \{H_\gamma | \gamma = 1, 2, \ldots, l\} = \{H_1, H_2, \ldots, H_l\}$;

(4.4) putting information of diagnosis support degrees of different diagnosis models into the same identification framework Θ to obtain a basic probability assignment; and (4.5) obtaining a compound probability assignment from the basic probability assignment to obtain confidence of different fault labels after fusion from the compound probability assignment, and using a fault label corresponding to a maximum confidence as a diagnosis result of the monitoring data to be diagnosed.

Preferably, the basic probability assignment is obtained by $$m_{k,\gamma} = \omega_k \xi_{k,\gamma}$$

$$m_{k,H} = m_k(H) = 1 - \sum_{\gamma=1}^{l} m_{k,\gamma} = 1 - \omega_k \sum_{\gamma=1}^{l} \xi_{k,\gamma}$$

$$\overset{\square}{m}_{k,H} = \overset{\square}{m}_k(H) = \omega_k \left(1 - \sum_{\gamma=1}^{l} \xi_{k,\gamma}\right)$$

$$\overline{m}_{k,H} = \overline{m}_k(H) = (1 - \omega_k),$$

where $\omega_k$ is a weight value the k-th diagnosis model, $m_{k,\gamma}$ represents the basic probability assignment of the k-th diagnosis model for the fault label $H_\gamma$ of a transformer, $m_k$ represents a function of calculating the basic probability assignment, and $m_{k,H}$ represents a residual probability assigned to an entire fault label set H.

Preferably, the compound probability assignment is obtained by $$\{H_\gamma\}: m_\gamma = K\left[\prod_{k=1}^{2}\left(m_{k,\gamma} + \overline{m}_{k,H} + \overset{\square}{m}_{k,H}\right) - \prod_{k=1}^{2}\left(\overline{m}_{k,H} + \overset{\square}{m}_{k,H}\right)\right],$$

where $m_\gamma$ represents the compound probability assignment of the fault label $H_\gamma$, K is an intermediate variable, and a normalized probability assignment $\xi_\gamma$ of the fault label $H_\gamma$ is calculated by $$\xi_\gamma = \frac{m_\gamma}{1 - \overline{m}_H}, \gamma = 1, \ldots, l$$

$$\overline{m}_H = K\left[\prod_{k=1}^{2}(\overline{m}_{k,H})\right],$$

and then a label corresponding to a maximum probability is output as the final diagnosis result according to the maximum confidence principle.

According to another aspect of the disclosure, a deep parallel fault diagnosis system for dissolved gas in transformer oil is provided, including:

a data processing module configured to obtain multiple groups of monitoring data of dissolved gas in each transformer oil, analyze a dissolved gas content in each of the groups of monitoring data, obtain a corresponding fault type label, perform a normalizing processing on each of the groups of monitoring data, and forming a target data set by combining the normalized groups of monitoring data with the corresponding fault type label;

a first training module configured to divide the target data set into a first training set and a first verification set, train a long short-term memory (LSTM) diagnosis model with the first training set, and verify the trained LSTM diagnosis model with the first verification set;

a second training module configured to perform image processing on each group of data in the target data set to obtain an image data set, divide the image data set into a second training set and a second verification set, train a convolutional neural network (CNN) diagnosis model with the second training set, and verify the trained CNN diagnosis model with the second verification set; and a diagnosis module configured to perform a deep parallel fusion on outputs of softmax layers of the trained LSTM diagnosis model and the trained CNN diagnosis model, respectively, and output a final diagnosis result according to a maximum confidence principle.

According to another aspect of the disclosure, a computer-readable storage medium with program instructions stored thereon is provided, and the deep parallel fault diagnosis method of dissolved gas in transformer oil as described in any of the above paragraphs is implemented by executing the program instructions by a processor.

In general, compared with the conventional technology, the above technical solutions provided by the disclosure can achieve the following beneficial effects: the disclosure makes full use of the ability of different deep learning methods to extract complex nonlinear features, and effectively improves the transformer fault diagnosis accuracy. The adopted feature parameters may obtain a higher diagnosis accuracy without complex feature design, and have a higher applicability.

DESCRIPTION OF THE EMBODIMENTS

In order to make the objectives, technical solutions, and advantages of the disclosure clearer, hereinafter, the disclosure will be further described in detail with reference to the accompanying drawings and embodiments. It should be understood that the specific embodiments described herein are only used to explain the disclosure, but are not intended to limit the disclosure. In addition, the technical features involved in various embodiments of the disclosure described below may be combined with each other as long as they do not conflict with each other.

In the embodiments of the disclosure, "first," "second," and the like are used to distinguish different objects, and do not have to describe a specific order or sequence.

The disclosure provides a deep parallel fault diagnosis method for dissolved gas in transformer oil. First, a DGA fault data set is collected, and normalizing and image processing are performed on the data; then, a new data set is used to train and verify LSTM and CNN diagnosis networks, respectively, to obtain required LSTM and CNN fault diagnosis networks for DGA; lastly, output layers of the two deep learning networks are removed, and a deep parallel fusion is performed on outputs of softmax layers by using a multi-source information fusion of a DS evidence theory, and a fault label corresponding a maximum confidence in fusion results is taken as a diagnosis result. This deep parallel fusion method makes full use of the ability of different deep learning methods to extract complex nonlinear features, and effectively improves the transformer fault diagnosis accuracy. The adopted feature parameters may achieve a higher diagnosis accuracy without complex feature design, and have a higher applicability.

Figure 1:
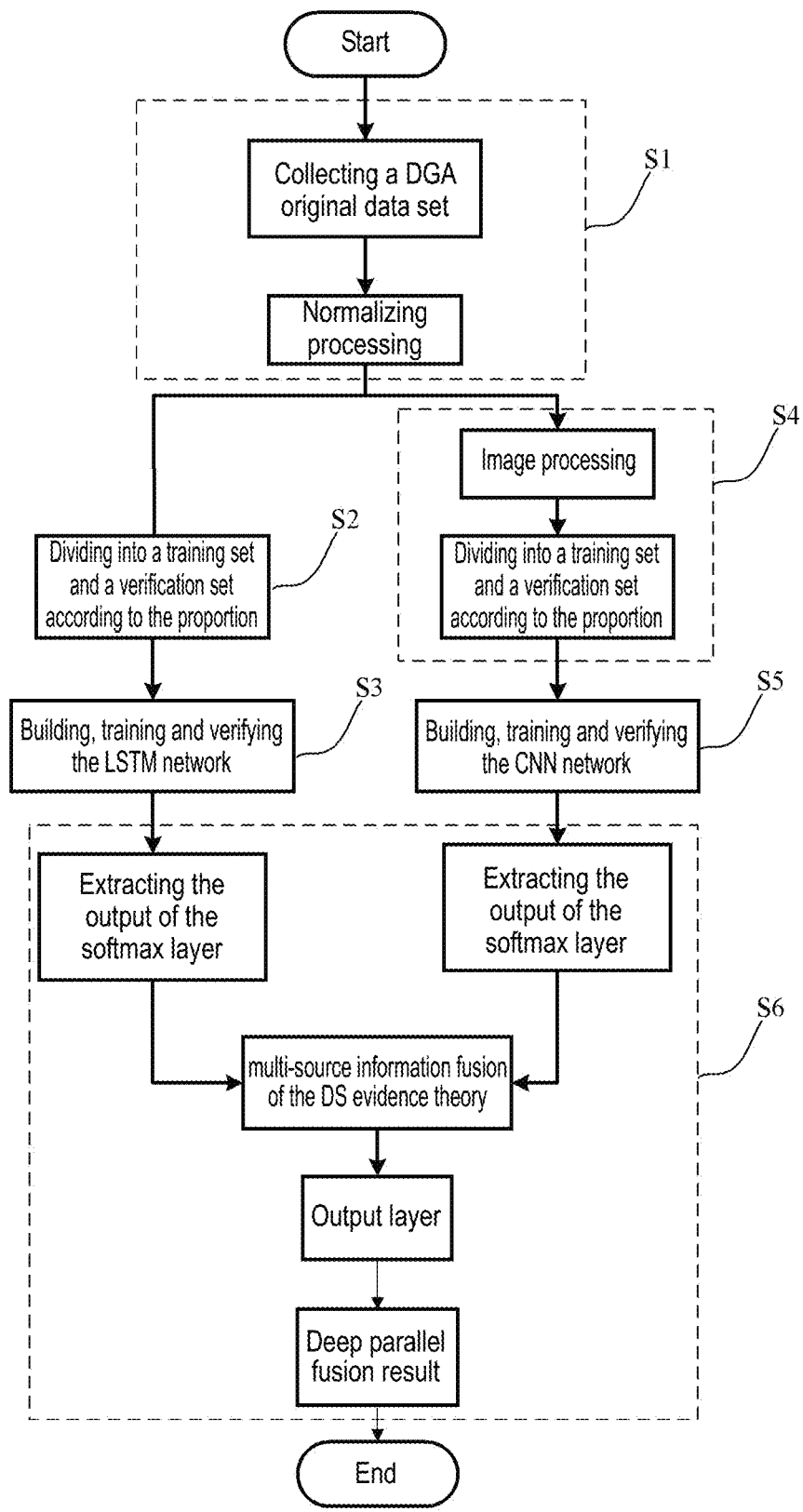
FIG. 1 is a schematic flow chart of a deep parallel fault diagnosis method for dissolved gas in transformer oil according to an embodiment of the disclosure.

FIG. 1 is a schematic flow chart of a deep parallel fault diagnosis method for dissolved gas in transformer oil according to an embodiment of the disclosure. As shown in FIG. 1, the deep parallel fault diagnosis method includes the following steps:

S1: Monitoring data of dissolved gas in each transformer oil is collected, and a dissolved gas content in the transformer oil is analyzed to obtain a corresponding fault label, and a normalizing processing is performed on the monitoring data.

In the embodiment of the disclosure, the data may be taken from relevant documents over the years and actual test data of power companies. Each group of data includes the contents of five key state parameters—hydrogen ($H_2$), methane ($CH_4$), ethane ($C_2H_6$), ethylene ($C_2H_4$), and acetylene ($C_2H_2$)—and their corresponding transformer states.

In the embodiment of the disclosure, the monitoring data of the dissolved gas in step S1 may be expressed as:

$$data_i = \{a_{i,1}, a_{i,2}, \ldots, a_{i,2}, \ldots, a_{i,N}, s_i\} i \in [1,K]$$

where K is K groups of monitoring data of the dissolved gas, $a_{i,j}$ is a content of the $j(j \in [1, N])$-th gas parameter in the i-th group of monitoring data of the dissolved gas, $s_i$ is a transformer state corresponding to the i-th group of monitoring data of the dissolved gas, and N is the number of gas types.

As an optional implementation way, the normalization method in step S1 may adopt Formula (1) for calculation:

$$z_i = \frac{X_i - E(X)}{D(X)} \quad (1)$$

where $X_i$ is a data sample, $E(X)$ is the mean, $D(X)$ is the variance, and $z_i$ is the regularized value.

The data obtained after normalization is expressed as:

$$data_i' = \{b_{i,1}, b_{i,2}, \ldots, b_{i,j}, \ldots, b_{i,N}, s_i\} i \in [1,K]$$

where K is K groups of monitoring data of dissolved gas, $b_{i,j}$ is the normalized value of the content of the $j(j \in [1,N])$-th gas parameter in the normalized i-th group of monitoring data of the dissolved gas, and $s_i$ is a transformer state corresponding to the i-th group of monitoring data of the dissolved gas.

In the embodiment of the disclosure, according to the commonly used IEC60599 standard, the transformer fault modes are divided into 6 types, namely high temperature overheating, medium temperature overheating, low temperature overheating, partial discharge, low energy discharge, and high energy discharge, as shown in Table 1:

TABLE 1

Fault mode coding

| Fault label | Fault type | Total number of samples | Training sample | Test sample |
|---|---|---|---|---|
| I | High temperature overheating | 232 | 186 | 46 |
| II | Medium temperature overheating | 240 | 192 | 48 |
| III | Low temperature overheating | 245 | 196 | 49 |
| IV | Partial discharge | 237 | 190 | 47 |
| V | Low energy discharge | 240 | 192 | 48 |
| VI | High energy discharge | 243 | 195 | 48 |
| | Total | 1437 | 1151 | 286 |

S2: The dissolved gas in the oil is used to build feature parameters, and the normalized new data set is divided into a training set and a verification set according to the proportion as the input of the LSTM diagnosis model.

The input data set obtained in step S2 is divided into two parts, in which n % is taken as the training set to train the LSTM network, and (1−η%) is taken as the test set to verify the accuracy of the transformer DGA fault diagnosis. For example, 80% is used as the training set to train a Bi-LSTM network, and 20% is used as the verification set to verify the diagnosis effect of the network on the LSTM diagnosis model.

S3: The LSTM diagnosis model is built, and the training set and the verification set are input for network training.

Figure 2:
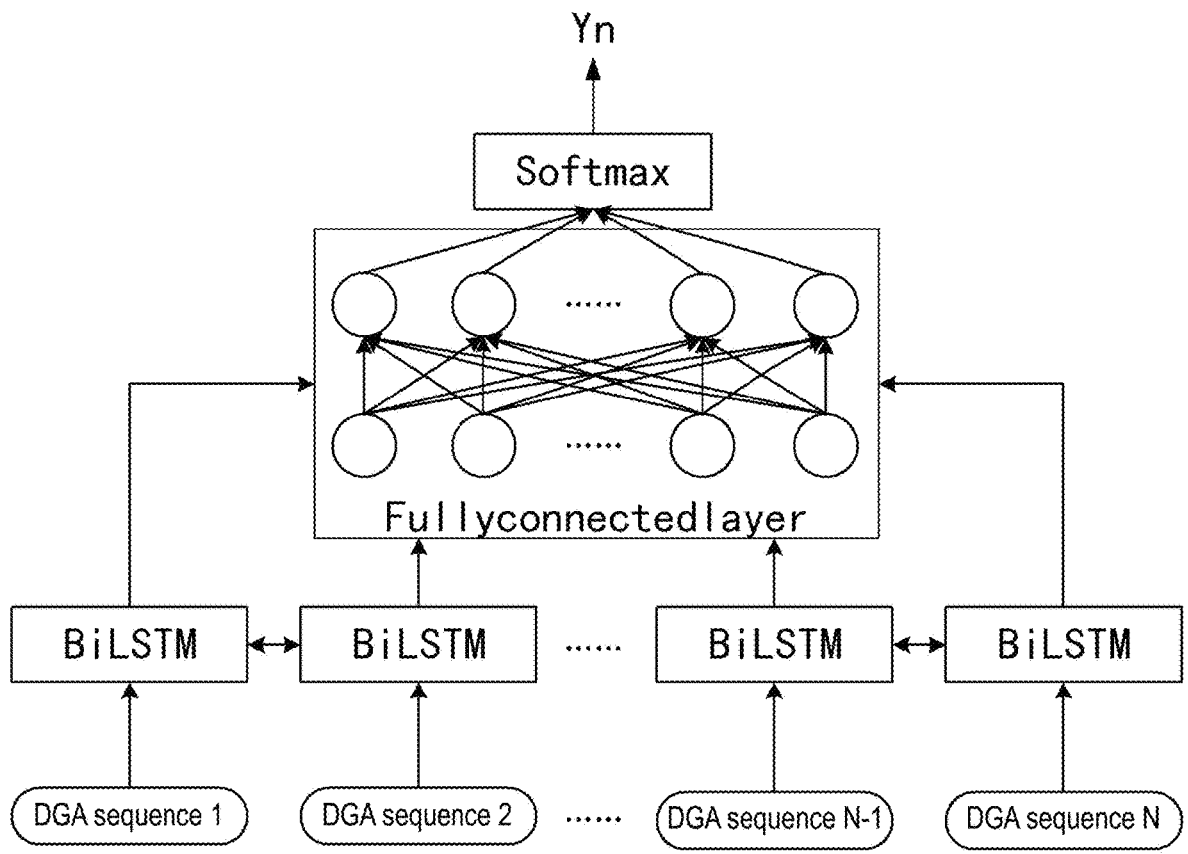
FIG. 2 is a schematic structure diagram of an LSTM network according to an embodiment of the disclosure.

In step S3, the specific method for building an LSTM-based deep learning framework is:

to build a five-layer network, as shown in FIG. 2, including an input layer, an LSTM layer, a fully connected layer, a softmax layer, and a classification output layer. The LSTM layer has multiple hidden units, and a state activation function thereof is "tanh," and a gate activation function thereof is "sigmoid." The hyperparameter setting of the network are shown in Table 2.

TABLE 2

Hyperparameter setting of LSTM network

| Name | Value |
|---|---|
| Optimizer | Adam |
| Gradient threshold | 0.01 |
| Number of hidden units | 150 |
| Minibatchsize | 100 |
| Maxepoch | 500 |

The softmax layer takes an output of the fully connected layer in the LSTM diagnosis model as an input vector, and outputs a diagnosis support degree of the LSTM diagnosis model for a fault label, specifically as follows:

$$Softmax(x_1) = \begin{bmatrix} \xi(H=1, x_1 | \theta) \\ \xi(H=2, x_1 | \theta) \\ \vdots \\ \xi(H=N, x_1 | \theta) \end{bmatrix} = \frac{1}{\sum_{i=1}^{N} e^{\theta_i^T x_1}} \begin{bmatrix} e^{\theta_1^T x_1} \\ e^{\theta_2^T x_1} \\ \vdots \\ e^{\theta_N^T x_1} \end{bmatrix}$$

where $x_1$ represents the output of the fully connected layer in the LSTM diagnosis model (that is, the input of the softmax layer), $\theta_i$, i=1, 2, . . . , N is a weight matrix of the softmax layer in the LSTM diagnosis model, and Softmax is an activation function.

S4: The dissolved gas in the oil is used to build the feature parameters, and image processing is performed on the data to obtain the image data set, and the image data set is divided into a training set and a verification set according to the proportion as the input of the CNN diagnosis model.

As an optional implementation way, in step S4, image processing is performed on the data, and differences of the data are presented in image with color and height, respectively, to obtain an image data set A and an image data set B, respectively, and an image is taken respectively from the image data set A and the image data set B, and expressed as:

data$_i''$={$c_i, s_i$}i∈[1,K], where K is K groups of monitoring data of the dissolved gas, $c_i$ is an image of a parameter conversion of the i-th group of monitoring data of the dissolved gas in the image data set A, and $s_i$ is a transformer state corresponding to the i-th group of monitoring data of the dissolved gas.

data$_i'''$={$d_i, s_i$}i∈[1,K], where K is K groups of monitoring data of the dissolved gas, $d_i$ is an image of a parameter conversion of the i-th group of monitoring data of the dissolved gas in the image data set B, and $s_i$ is a transformer state corresponding to the i-th group of monitoring data of the dissolved gas.

S5: The CNN diagnosis model is built, and the training set and the verification set are input to train the CNN diagnosis model; if the amount of data is large enough, the most basic CNN diagnosis model may be built, and big data may be used to train and verify the CNN diagnosis model, and if the amount of data is small, transfer learning may be used for transfer training and verification of classic models such as MobileNet-V2.

In the embodiment of the disclosure, the CNN diagnosis model may also use other models, and the embodiment of the disclosure does not pose any specific limitation.

Figure 3:
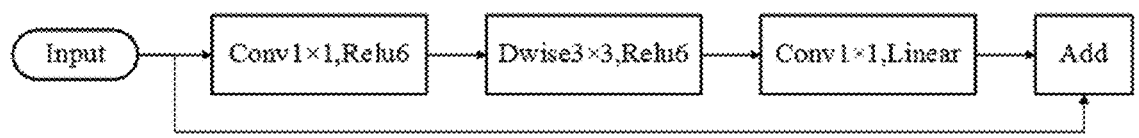
FIG. 3 is a schematic structure diagram of a CNN unit according to an embodiment of the disclosure.
Figure 3:

FIG. 3 is a schematic structure diagram of a CNN unit according to an embodiment of the disclosure. As shown in FIG. 3, the specific details are as follows.

MobileNet-V2 is built based on the basic concepts of MobileNet-V1. MobileNet-V2 proposes two innovative design ideas: inverted residuals and linear bottlenecks.

Inverted residuals: Before the depth-wise convolution of MobileNet-V2, there is a 1×1 "expansion" layer, whose purpose is to expand the number of channels in the data before the data enters the deep convolution, to enrich the number of features, and to improve accuracy.

Linear bottlenecks: MobileNet-V2 proposes to replace a ReLU activation function with a linear activation function after layers with a smaller number of channels. Because of the introduction of the "expansion layer," a large number of features output by the convolutional layer need to be "compressed" to reduce the amount of calculation. As the number of channels decreases, if the activation function still selects ReLu, the features will be destroyed. This is because the output of ReLu is all zero for negative input; as the original features have been "compressed," further features will be "lost" after undergoing ReLu.

Specifically, the softmax layer takes the output of the fully connected layer in the CNN diagnosis model as the input vector, and outputs a diagnosis support degree of the CNN diagnosis model for a fault label, specifically as follows:

$$Softmax(x_2) = \begin{bmatrix} \xi(H=1, x_2 \mid \theta) \\ \xi(H=2, x_2 \mid \theta) \\ \vdots \\ \xi(H=N, x_2 \mid \theta) \end{bmatrix} = \frac{1}{\sum_{i=1}^{N} e^{\theta_i'^T x_2}} \begin{bmatrix} e^{\theta_1'^T x_2} \\ e^{\theta_2'^T x_2} \\ \vdots \\ e^{\theta_N'^T x_2} \end{bmatrix}$$

where $x_2$ represents the output of the fully connected layer in the CNN diagnosis model (that is, the input of the softmax layer), $\theta'_i$, i=1, 2, ..., N is a weight matrix of the softmax layer in the CNN diagnosis model, and Softmax is an activation function.

Figure 4:
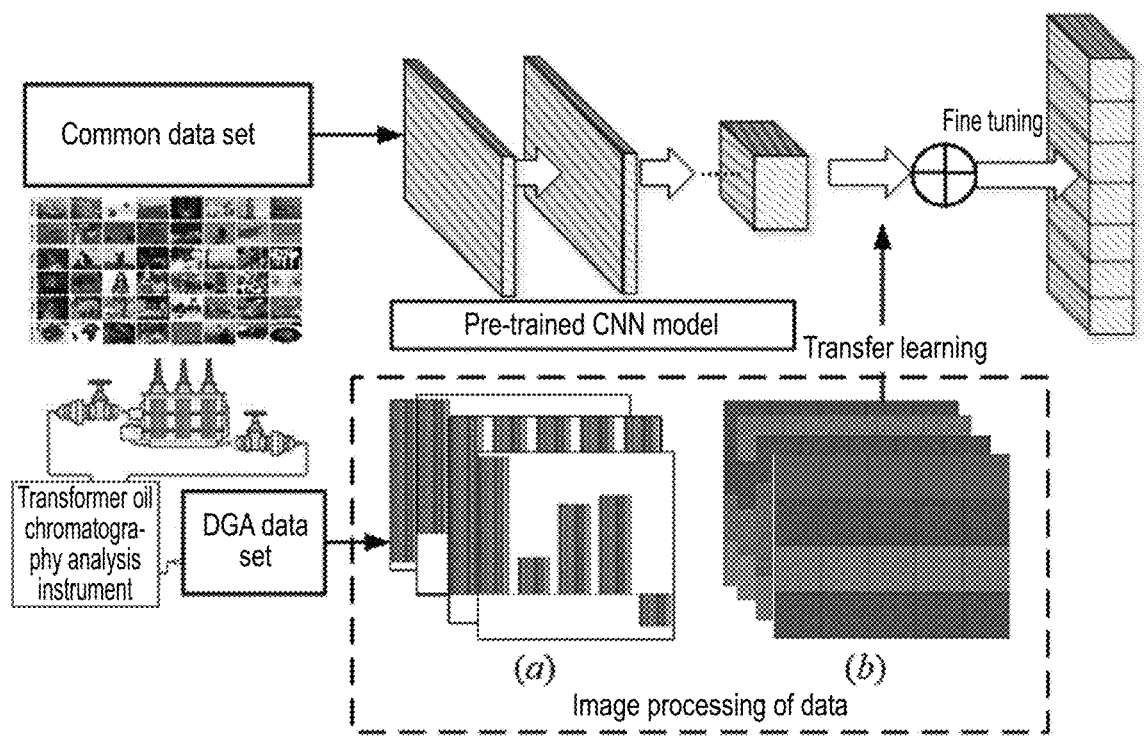
FIG. 4 is a schematic diagram of data visualization and CNN transfer training according to an embodiment of the disclosure.

As an optional implementation way, as shown in FIG. 4, step S5 uses transfer learning to perform transfer training and verification on the classic model MobileNet-V2. First, the last fully connected layer of MobileNet-V2 is replaced to make its number of outputs equal to the number of diagnosis label types, which is 6 in this embodiment. Then, the parameters of the first 50% of the pre-training network are freezed, and lastly the hyperparameter of the transfer training based on the MobileNet-V2 model are set as shown in Table 3, and the training set is input to train the unfrozen part of the network.

TABLE 3

| Hyperparameter setting of CNN diagnosis model | |
| --- | --- |
| Name | Value |
| Optimizer | Adam |
| Initial gradient | 0.003 |
| Initial learning rate | 3e−4 |
| Weight learning rate | 10 |
| Offset learning rate | 10 |
| Minibatchsize | 30 |
| Maxepoch | 60 |

S6: The DS evidence theory is used to perform a deep parallel fusion of outputs of the softmax layers of the two deep learning models, and the final diagnosis result is output through the output layer.

Figure 5:
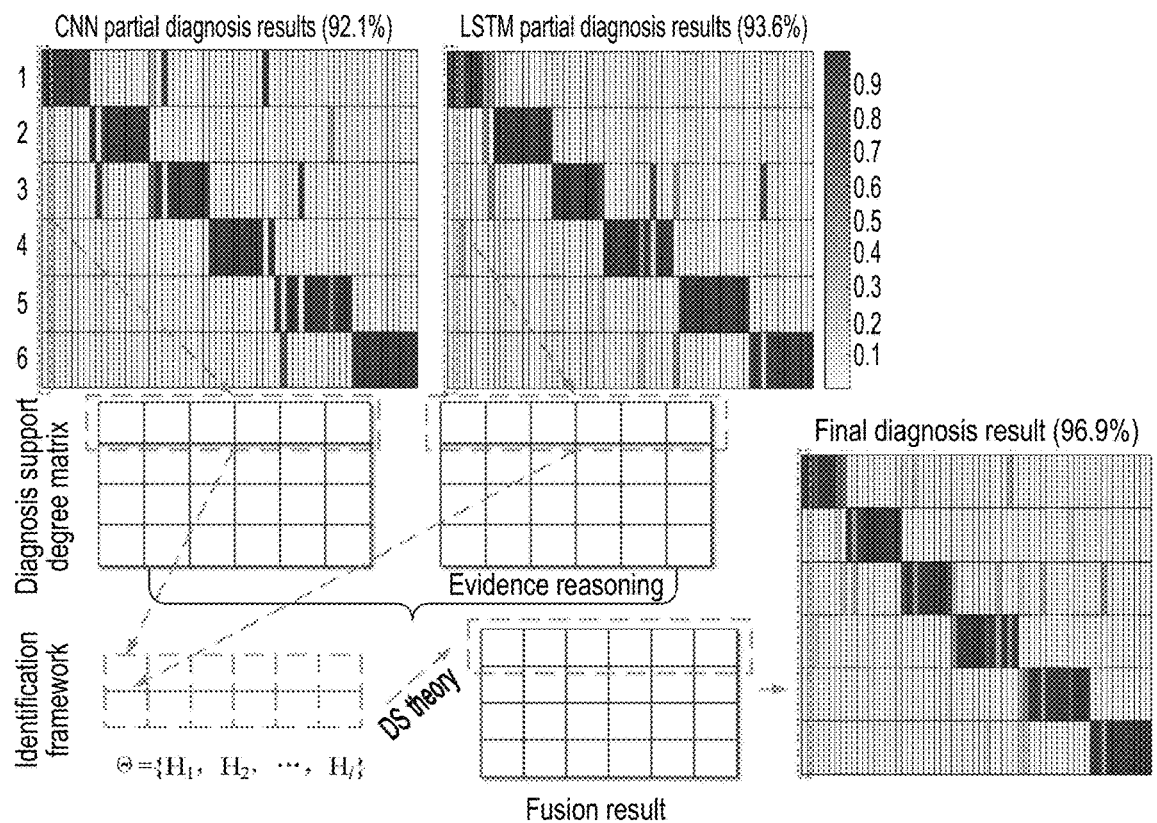
FIG. 5 is a schematic diagram of a deep parallel fusion according to an embodiment of the disclosure.

As an optional implementation way, in step S6, the deep parallel fusion uses the DS evidence theory to fuse the diagnosis support degrees for fault labels output by the softmax layers of the CNN and LSTM diagnosis networks. As shown in FIG. 5, step S6 may be implemented specifically in the following way:

(1) obtaining the output of the softmax layer of each deep learning diagnosis network, that is, the diagnosis support degrees of CNN and LSTM for fault labels corresponding to the same group of DGA monitoring data: $\xi_{k,\gamma}=\xi_{k,1}$, $\xi_{k,2}, \ldots, \xi_{k,l}$, (the value of k represents different methods, and l is the total number of fault labels, that is, $\gamma=1, 2, \ldots, l$);

(2) taking different methods k as rows and the diagnosis support degrees $\xi_{k,\gamma}$ as columns to form a support degree matrix, that is, $\{(H_\gamma, \xi_{k,\gamma}), k=1, 2, \gamma=1, \ldots, l\}$, where each element of the support degree matrix represents that the support degree of the k-th diagnosis method for a fault label $H_\gamma$ is $\xi_{k,\gamma}$;

(3) treating each column in the support degree matrix as an identification framework $\Theta$ of a DS evidence theory, thus $\Theta=\{H_\gamma|\gamma=1, 2, \ldots, l\}=\{H_1, H_2, \ldots, H_l\}$;

(4) putting information of diagnosis support degrees of different diagnosis methods into the same identification framework $\Theta$ to calculate a basic probability assignment m (BPA);

$$m_{k,\gamma} = m_k(H_\gamma) = \omega_k \xi_{k,\gamma} \quad (2)$$

$$m_{k,H} = m_k(H) = 1 - \sum_{\gamma=1}^{l} m_{k,\gamma} = 1 - \omega_k \sum_{\gamma=1}^{l} \xi_{k,\gamma} \quad (3)$$

$$\overset{\square}{m}_{k,H} = \overset{\square}{m}_k(H) = \omega_k\left(1 - \sum_{\gamma=1}^{l} \xi_{k,\gamma}\right) \quad (4)$$

$$\overline{m}_{k,H} = \overline{m}_k(H) = (1 - \omega_k) \quad (5)$$

where $\omega_k$ is the weight value of each diagnosis method k (k=1, 2), and generally, the average value may be taken, that is, $\omega_k=\frac{1}{2}$; $m_{k,\gamma}$ represents the basic probability assignment of the k-th method for the evaluation target (that is, the fault state of the transformer) $H_\gamma$; $m_k$ represents the function of calculating the basic probability assignment; $m_{k,H}$ represents the residual probability assigned to the entire fault label set H, rather than to a specific transformer fault state; and $\overset{\square}{m}_{k,H}$ and $\overline{m}_{k,H}$ are intermediate variables used to calculate the basic probability assignment.

(5) Compound probability assignment:

$$\{H_\gamma\}:m_\gamma = K\left[\prod_{k=1}^{2}\left(m_{k,\gamma} + \overline{m}_{k,H} + \overset{\square}{m}_{k,H}\right) - \prod_{k=1}^{2}\left(\overline{m}_{k,H} - \overset{\square}{m}_{k,H}\right)\right] \quad (6)$$

$$\{H\}:\overset{\square}{m}_H = K\left[\prod_{k=1}^{2}\left(\overline{m}_{k,H} + \overset{\square}{m}_{k,H}\right) - \prod_{k=1}^{2}\left(\overline{m}_{k,H}\right)\right] \quad (7)$$

$$\{H\}:\overline{m}_H = K\left[\prod_{k=1}^{2}\left(\overline{m}_{k,H}\right)\right] \quad (8)$$

$$K = \left[\sum_{\gamma=1}^{l}\prod_{k=1}^{2}\left(m_{k,\gamma} + \overline{m}_{k,H} + \overset{\square}{m}_{k,H}\right) - (l-1)\prod_{k=1}^{2}\left(\overline{m}_{k,H} + \overset{\square}{m}_{k,H}\right)\right]^{-1} \quad (9)$$

where $m_\gamma$ represents the compound probability assignment of the fault label, and K, $m_{k,H}$ and $\overline{m}_H$ are intermediate variables used to calculate the compound probability assignment.

Lastly, a normalizing processing is performed to obtain the synthesized diagnosis result:

$$\xi_\gamma = \frac{m_\gamma}{1 - \overline{m}_H}, \gamma = 1, \ldots, l \quad (10)$$

$$\xi_\gamma = \frac{\overset{\square}{m}_H}{1 - \overline{m}_H}, \gamma = 1, \ldots, l \quad (11)$$

That is, $\xi_\gamma, \gamma=1, \ldots, l$ is the normalized result of the confidence of different fault labels obtained by the fusion, and $\xi_\gamma$ represents the normalized value of the uncertainty distribution.

Lastly, the fault label corresponding to the maximum confidence is output as the final diagnosis result.

In the end, in the models in this embodiment, the LSTM fault diagnosis accuracy is 93.6%, and the CNN fault diagnosis accuracy is 92.1%, and the deep parallel diagnosis accuracy is 96.9%.

Figure 6:
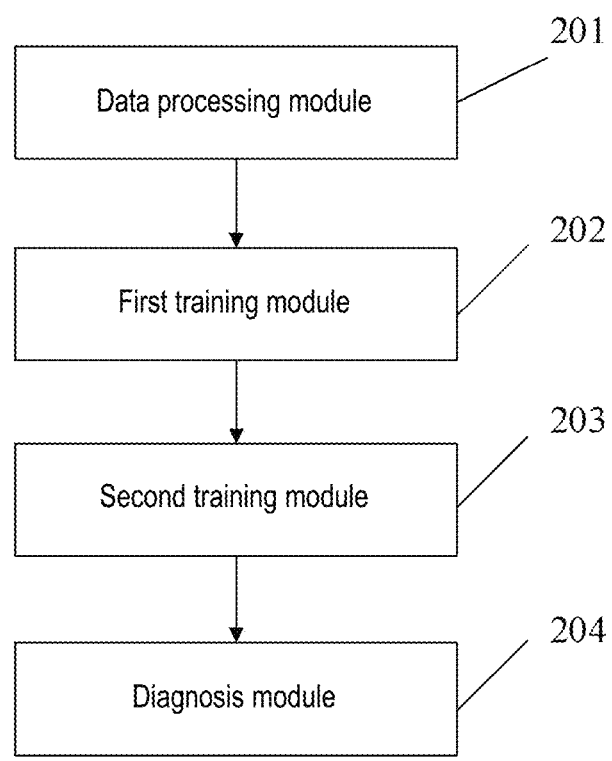
FIG. 6 is a schematic structure diagram of a system according to an embodiment of the disclosure.

FIG. 6 is a schematic structure diagram of a deep parallel fault diagnosis system for dissolved gas in transformer oil according to an embodiment of the disclosure. As shown in FIG. 6, the deep parallel fault diagnosis system includes:

a data processing module 201 configured to obtain multiple groups of monitoring data of dissolved gas in each transformer oil, analyze the dissolved gas content in each group of monitoring data, obtain a corresponding fault type label, perform a normalizing processing on each group of monitoring data, and forming a target data set by combining the normalized groups of monitoring data with the corresponding fault type label;

a first training module 202 configured to divide the target data set into a first training set and a first verification set, train the LSTM diagnosis model with the first training set, and verify the trained LSTM diagnosis model with the first verification set;

a second training module 203 configured to perform image processing on each group of data in the target data set to obtain an image data set, divide the image data set into a second training set and a second verification set, train the CNN diagnosis model with the second training set, and verify the trained CNN diagnosis model with the second verification set; and a diagnosis module 204 configured to perform a deep parallel fusion on the outputs of the softmax layers of the trained LSTM diagnosis model and the trained CNN diagnosis model, respectively, and output the final diagnosis result through the output layer.

Regarding the specific implementation of each module, reference may be made to the description of the method embodiment, and this embodiment of the disclosure will not repeat the details.

In another embodiment of the disclosure, a computer-readable storage medium is further provided, on which program instructions are stored, and when the program instructions are executed by a processor, the deep parallel fault diagnosis method of dissolved gas in transformer oil in the above method embodiment is implemented.

It should be noted that according to the needs of implementation, each step/component described in the disclosure may be split into more steps/components, or two or more steps/components or partial operations of steps/components may be combined into new steps/components to implement the disclosure.

The above method according to the disclosure may be implemented in hardware, firmware, or implemented as software or computer code that may be stored in a recording medium (such as a CD ROM, a RAM, a floppy disk, a hard disk, or a magneto-optical disk), or by downloading through the network the computer code originally stored in a remote recording medium or non-transitory machine-readable medium and storing in a local recording medium, so that the method described herein may be processed by such software stored on a recording medium using a general-purpose computer, a dedicated processor, or programmable or dedicated hardware (such as an ASIC or a FPGA). It may be understood that a computer, a processor, a microprocessor controller, or programmable hardware includes a storage component (such as a RAM, a ROM, a flash memory and the like) that may store or receive software or computer code, and when the software or the computer code is accessed and executed by a computer, a processor or hardware, the processing method described herein is implemented. In addition, when a general-purpose computer accesses the code for implementing the processing described herein, the execution of the code converts the general-purpose computer into a dedicated computer for executing the processing described herein.

People skilled in the art may easily understand that the above descriptions are only exemplary embodiments of the disclosure and are not intended to limit the disclosure. Any modification, equivalent replacement, improvement and the like made within the spirit and principle of the disclosure shall all be included in the protection scope of the disclosure.

What is claimed is:

1. A deep parallel fault diagnosis method for dissolved gas in transformer oil, comprising following steps executing by a processor:

step 1: performing an operation of a plurality of transformers of a power system of a power grid and obtaining a plurality of groups of monitoring data of dissolved gas in each transformer oil of the plurality of transformers of the power system of the power grid, analyzing a dissolved gas content in each of the groups of monitoring data, obtaining a corresponding fault type label, performing a normalizing processing on each of the groups of monitoring data, and forming a target data set by combining the normalized groups of monitoring data with the corresponding fault type label;

step 2: dividing the target data set into a first training set and a first verification set, training a long short-term memory (LSTM) diagnosis model with the first training set, and verifying the trained LSTM diagnosis model with the first verification set;

step 3: performing image processing on each group of data in the target data set to obtain an image data set, dividing the image data set into a second training set and a second verification set, training a convolutional neural network (CNN) diagnosis model with the second training set, and verifying the trained CNN diagnosis model with the second verification set;

step 4: performing a deep parallel fusion on outputs of softmax layers of the trained LSTM diagnosis model and the trained CNN diagnosis model, respectively, and outputting a final diagnosis result according to a maximum confidence principle; and step 5: modifying the operation of the plurality of transformers of the power system of the power grid based on the final diagnosis result.

2. The method according to claim 1, wherein the groups of monitoring data of the dissolved gas in each transformer oil are $data_i=\{a_{i,1}, a_{i,2}, \ldots, a_{i,j}, \ldots, a_{i,N}, s_i\}$ $i\in[1,K]$, where K is K groups of monitoring data of the dissolved gas, $a_{i,j}$ is a content of the $j(j\in[1,N])$-th gas parameter in the i-th group of monitoring data of the dissolved gas, $s_i$ is a transformer state corresponding to the i-th group of monitoring data of the dissolved gas, and N is the number of gas types, and data obtained after normalization is $data_i'=\{b_{i,1}, b_{i,2}, \ldots, b_{i,j}, \ldots, b_{i,N}, s_i\}$ $i\in[1,K]$, where K is K groups of monitoring data of the dissolved gas, $b_{i,j}$ is a normalized value of the content of the $j(j\in[1,N])$-th gas parameter in the i-th group of monitoring data of the dissolved gas, $s_i$ is the transformer state corresponding to the i-th group of monitoring data of the dissolved gas, and N is the number of gas types.

3. The method according to claim 2, wherein the LSTM diagnosis model comprises:

an input layer;

an LSTM layer;

a fully connected layer;
the softmax layer; and
a classification output layer,
wherein the LSTM layer comprises a plurality of hidden units, and a state activation function of the hidden units is tanh, and a gate activation function of the hidden units is sigmoid, and
the softmax layer takes an output of the fully connected layer in the LSTM diagnosis model as an input vector and obtains a diagnosis support degree of the LSTM diagnosis model for a fault label by $$Softmax(x_1) = \frac{1}{\sum_{i=1}^{N} e^{\theta_i^T x_1}} \begin{bmatrix} e^{\theta_1^T x_1} \\ e^{\theta_2^T x_1} \\ \vdots \\ e^{\theta_N^T x_1} \end{bmatrix},$$

where $x_1$ represents the output of the fully connected layer in the LSTM diagnosis model, $\theta_i$, i=1, 2, ..., N is a weight matrix of the softmax layer in the LSTM diagnosis model, and Softmax is an activation function.

4. The method according to claim 3, wherein performing image processing on each group of data in the target data set to obtain the image data set in the step 3 comprises:
performing image processing on each group of data in the target data set, presenting differences of the data in image with color to obtain an image data set A and presenting differences of the data in image with height to obtain an image data set B, respectively,
wherein the image data set A is expressed as $data_i''=\{c_i,s_i\}$ $i \in [1,K]$, and the image data set B is expressed as $data_i'''=\{d_i,s_i\}$ $i \in [1,K]$, where K is K groups of monitoring data of the dissolved gas, $c_i$ is an image of a parameter conversion of the i-th group of monitoring data of the dissolved gas in the image data set A, $d_i$ is an image of a parameter conversion of the i-th group of monitoring data of the dissolved gas in the image data set B, and $s_i$ is the transformer state corresponding to the i-th group of monitoring data of the dissolved gas.

5. The method according to claim 4, wherein the softmax layer in the CNN diagnosis model takes an output of a fully connected layer in the CNN diagnosis model as an input vector, and obtains a diagnosis support degree for a fault label by $$Softmax(x_2) = \frac{1}{\sum_{i=1}^{N} e^{\theta_i'^T x_2}} \begin{bmatrix} e^{\theta_1'^T x_2} \\ e^{\theta_2'^T x_2} \\ \vdots \\ e^{\theta_N'^T x_2} \end{bmatrix},$$

where $x_2$ represents the output of the fully connected layer in the CNN diagnosis model, $\theta'_i$, i=1, 2, ..., N is a weight matrix of the softmax layer in the CNN diagnosis model, and Softmax is an activation function.

6. The method according to claim 5, wherein the step 4 comprises:
step 4.1: obtaining diagnosis support degrees of the softmax layers of the LSTM diagnosis model and the CNN diagnosis model for fault labels corresponding to the same group of monitoring data to be diagnosed: $\xi_{k,\gamma}=\xi_{k,1}, \xi_{k,2}, \ldots, \xi_{k,l}$, where the value of k represents different diagnosis models, l is the total number of fault labels, and $\gamma=1, 2, \ldots, l$;

step 4.2: taking different diagnosis models k as rows and the diagnosis support degrees $\xi_{k,\gamma}$ as columns to form a support degree matrix $\{(H_\gamma,\xi_{k,\gamma}), k=1, 2, \gamma=1, \ldots, l\}$, where each element of the support degree matrix represents that the support degree of the k-th diagnosis model for a fault label $H_\gamma$ is $\xi_{k,\gamma}$;

step 4.3: treating each column in the support degree matrix as an identification framework $\Theta$ of a DS evidence theory, thus $\Theta=\{H_\gamma|\gamma=1, 2, \ldots, l\}=\{H_1, H_2, \ldots, H_l\}$;

step 4.4: putting information of diagnosis support degrees of different diagnosis models into the same identification framework $\Theta$ to obtain a basic probability assignment; and step 4.5: obtaining a compound probability assignment from the basic probability assignment to obtain confidence of different fault labels after fusion from the compound probability assignment, and using a fault label corresponding to a maximum confidence as a diagnosis result of the monitoring data to be diagnosed.

7. The method according to claim 6, wherein the basic probability assignment is obtained by $$m_{k,\gamma} = \omega_k \xi_{k,\gamma}$$

$$m_{k,H} = m_k(H) = 1 - \sum_{\gamma=1}^{l} m_{k,\gamma} = 1 - \omega_k \sum_{\gamma=1}^{l} \xi_{k,\gamma}$$

$$\overset{\square}{m}_{k,H} = \overset{\square}{m}_k(H) = \omega_k\left(1 - \sum_{\gamma=1}^{l} \xi_{k,\gamma}\right),$$

$$\overline{m}_{k,H} = \overline{m}_k(H) = (1 - \omega_k)$$

where $\omega_k$ is a weight value the k-th diagnosis model, $m_{k,\gamma}$ represents the basic probability assignment of the k-th diagnosis model for the fault label $H_\gamma$ of a transformer, $m_k$ represents a function of calculating the basic probability assignment, and $m_{k,H}$ represents a residual probability assigned to an entire fault label set H.

8. The according to claim 7, wherein the compound probability assignment is obtained by $$\{H_\gamma\}:m_\gamma = K\left[\prod_{k=1}^{2}\left(m_{k,\gamma} + \overline{m}_{k,H} + \overset{\square}{m}_{k,H}\right) - \prod_{k=1}^{2}\left(\overline{m}_{k,H} + \overset{\square}{m}_{k,H}\right)\right],$$

where $m_\gamma$ represents the compound probability assignment of the fault label $H_\gamma$, K is an intermediate variable, and
a normalized probability assignment $\xi_\gamma$ of the fault label $H_\gamma$ is calculated by $$\xi_\gamma = \frac{m_\gamma}{1 - \overline{m}_H}, \gamma = 1, \ldots, l$$

$$\overline{m}_H = K\left[\prod_{k=1}^{2}(\overline{m}_{k,H})\right]$$

and a label corresponding to a maximum probability is output as the final diagnosis result according to the maximum confidence principle.

9. A computer-readable non-transitory storage medium with program instructions stored thereon, wherein the deep parallel fault diagnosis method of dissolved gas in transformer oil according to claim 1 is implemented by executing the program instructions by the processor.

10. A computer-readable non-transitory storage medium with program instructions stored thereon, wherein the deep parallel fault diagnosis method of dissolved gas in transformer oil according to claim 2 is implemented by executing the program instructions by the processor.

11. A computer-readable non-transitory storage medium with program instructions stored thereon, wherein the deep parallel fault diagnosis method of dissolved gas in transformer oil according to claim 3 is implemented by executing the program instructions by the processor.

12. A computer-readable non-transitory storage medium with program instructions stored thereon, wherein the deep parallel fault diagnosis method of dissolved gas in transformer oil according to claim 4 is implemented by executing the program instructions by the processor.

13. A computer-readable non-transitory storage medium with program instructions stored thereon, wherein the deep parallel fault diagnosis method of dissolved gas in transformer oil according to claim 5 is implemented by executing the program instructions by the processor.

14. A computer-readable non-transitory storage medium with program instructions stored thereon, wherein the deep parallel fault diagnosis method of dissolved gas in transformer oil according to claim 6 is implemented by executing the program instructions by the processor.

15. A computer-readable non-transitory storage medium with program instructions stored thereon, wherein the deep parallel fault diagnosis method of dissolved gas in transformer oil according to claim 7 is implemented by executing the program instructions by the processor.

16. A computer-readable non-transitory storage medium with program instructions stored thereon, wherein the deep parallel fault diagnosis method of dissolved gas in transformer oil according to claim 8 is implemented by executing the program instructions by the processor.

\* \* \* \* \*